United States Patent
Fasani

(10) Patent No.: US 6,293,928 B1
(45) Date of Patent: *Sep. 25, 2001

(54) CANNULA FOR VAGINAL IRRIGATIONS

(75) Inventor: Roberto Fasani, Bergamo (IT)

(73) Assignee: Medi Service S.r.l., Agrate Brianza (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/223,460

(22) Filed: Dec. 30, 1998

Related U.S. Application Data

(63) Continuation of application No. PCT/IT97/00194, filed on Jul. 29, 1997.

(51) Int. Cl.$^7$ .......................... A61M 31/00; A61M 5/00; A61M 3/02; B65D 5/72; B05B 7/00
(52) U.S. Cl. .......................... 604/279; 604/39; 604/181; 604/187; 604/257; 222/575; 222/630
(58) Field of Search .................................. 604/19, 27, 39, 604/181, 183, 185, 187, 212, 257, 261, 275, 279; 222/630–33, 566–69, 575, 570, 526–27

(56) References Cited

U.S. PATENT DOCUMENTS

| | | | |
|---|---|---|---|
| 693,358 | * | 2/1902 | Westlake . |
| 1,098,220 | * | 5/1914 | Borosody . |
| 2,087,511 | * | 7/1937 | Gould . |
| 2,139,653 | * | 12/1938 | Belfrage . |
| 2,596,597 | * | 5/1952 | Raymond et al. . |
| 4,329,990 | | 5/1982 | Sneider . |
| 4,336,801 | | 6/1982 | Sentell et al. . |
| 5,380,275 | * | 1/1995 | Kensey et al. ............ 604/27 |
| 5,857,991 | * | 1/1999 | Grothoff et al. ........... 604/2 |
| 5,858,010 | * | 1/1999 | Berry ....................... 604/279 |

FOREIGN PATENT DOCUMENTS 195 30 879 A1    2/1997   (DE) .

* cited by examiner

*Primary Examiner*—Angela D. Sykes
*Assistant Examiner*—Patricia Bianco
(74) *Attorney, Agent, or Firm*—Akin, Gump, Strauss, Hauer & Feld, L.L.P.

(57) ABSTRACT

A cannula for vaginal irrigations includes a straight cylindrical duct (1) whose proximal end is shaped to form a connection (4) for the mounting on a supplying device (5) containing a treating solution, as well as an ogive (2) extending rearwards from the distal end of said duct (1) so as to enclose externally the distal portion of the duct (1), whose distal end is in communication with the outside through a ring of at least four holes (3) formed on the tip of the ogive (2). The ogive (2) has an elliptical shape both in the longitudinal plane and in the plane orthogonal to the longitudinal axis and extends almost to mid-length of the duct (1), while the holes (3) are inclined at 30° with respect to the axis of the duct (1) both in the sagittal plane and in the longitudinal plane orthogonal thereto. The anatomical shape of the ogive (2) and the arrangement of the holes (3) provide an irrigation which is correct, effective and without risks for the user.

14 Claims, 2 Drawing Sheets

CANNULA FOR VAGINAL IRRIGATIONS

CROSS-REFERENCE TO RELATED APPLICATION

This application is a continuation of International Application PCT/IT97/00194, filed Jul. 29, 1997, the disclosure of which is incorporated herein by reference.

BACKGROUND OF THE INVENTION

The present invention relates to devices for female private hygiene, and in particular to a cannula for vaginal douche suitable to facilitate the carrying out of vaginal irrigations.

It is known that one of the most widespread practices for female private hygiene is the irrigation of the vagina with solutions having hygienic and/or therapeutic properties, i.e. products for periodical ablutions or medicaments for local treatments. In any case, prior art douches essentially consist of a bottle containing the solution and manufactured with an easily compressible structure, on which there is mounted a stiffer cannula to be inserted in the vagina.

The cannula is in practice a cylindrical tube, possibly tapered at the distal end, having a plurality of transverse holes, i.e. holes with their axes orthogonal to the longitudinal axis of the cannula. The proximal end of the cannula is provided with a connection for the mounting on the container, possibly in an inclined position with a 20°–30° angle so as to facilitate the insertion in the vagina. This inclination which is sometimes present is the only "concession" to the anatomy of the user, which for the rest often experiences troubles and difficulties due to the above-described structure of the cannula.

One of the most frequently experienced difficulties is the poor retention of the liquid inserted in the vagina, which clearly implies a poor efficacy of the treatment since the product does not remain in place for the time required to carry out its action. This is caused by the lack of adhesion between the cannula and the walls of the vaginal duct according to the tone and trophism of the latter, as well as by the poorly anatomical cylindrical shape of the cannula. As a remedy to this drawback, the user may carry out the irrigation in the bathtub in the supine position with her legs bent rather than simply crouched down or sitting on the bidet. As a matter of fact such a position favors the retention of the liquid in the vagina for a longer time, but on the other hand it requires the complete undressing, is more uncomfortable and a sufficiently long bathtub is needed.

Another frequent difficulty is the obstacle to the emission of the liquid from the cannula due to the transverse arrangement of the holes which may be temporarily obstructed by the contact with the vaginal walls. In fact, many users erroneously think that in the position taken for the irrigation the vaginal duct is directed upwards and consequently insert the cannula with the tip pointing upwards, where it meets the front vaginal wall which hinders a correct irrigation. On the contrary it results that, in both the above-mentioned positions, the vaginal duct is directed backwards and downwards, where it ends in the rear vaginal fornix which is the place of collection of most mucosa and inflammatory exudate. Therefore it is difficult to obtain with a conventional cannula an effective irrigation of the most delicate and treatment-requiring area which is located at the distal end of the vaginal duct, close to the cervix uteri.

However the most serious troubles which more hinder the use of conventional cannulae are pelvic pains and blood discharges, which are experienced both in concomitance with the irrigation and sometimes also in the following days. In these cases a shove occurs of the cannula tip against the portion of the cervix uteri projecting in the vaginal duct (portio). This mechanical stimulation often causes painful uterine contractions, especially in the presence of inflammatory conditions and other pre-existing troubles (ectopia of the portio, retroversion, etc.), which may accelerate the emission of blood already present in the uterus and/or favour the detachment of endometrium portions, and the shove itself may cause epithelial breakings of the vaginal walls or of an ectopia. Also in this instance, the structure of the conventional cannula proves inadequate for an irrigation which is correct, effective and without risks for the user.

SUMMARY OF THE INVENTION

Therefore the object of the present invention is to provide a cannula for vaginal irrigations which overcomes the above-mentioned drawbacks.

This object is achieved by means of a cannula having the characteristics disclosed in claim 1.

A first fundamental advantage of the cannula according to the present invention is given by the terminal ogive which is anatomically shaped to adhere to the walls of the vaginal duct, whereby the early downflow of the treating solution is dramatically reduced. This allows to keep the product in contact with the vaginal mucosae for a time suitable for the achievement of an effective treatment without necessarily making use of the supine position when carrying out the irrigation. This results in a greater proneness of women towards the vaginal irrigations since they can be easily carried out by crouching down or sitting on the bidet even in the less comfortable situations, according to the therapeutic or prophylactic indications (periodical or post-coitus irrigations).

A second significant advantage of the anatomical shape of the terminal ogive is that of allowing an easy insertion in the vulvar entrance and of preventing the undesirable mechanical stimulation of the portio. In this way, the troubles which most worry the users, i.e. pelvic pains and blood discharges, are prevented.

A further advantage of the present cannula stems from the arrangement at its distal end of the holes for the emission of the treating solution. The position and inclination of said holes allow the emission of a jet of liquid which adequately reaches the rear vaginal fornix, whereby it acts in the area which mostly requires the treatment. Furthermore, the obstacle to the emission of the liquid caused by the lateral contact with the vaginal walls is avoided, thanks both to the nearly axial orientation of the holes and to their arrangement at the tip of the ogive which keeps away the vaginal walls.

These and other advantages and characteristics of the cannula for vaginal irrigations according to the present invention will be clear to those skilled in the art from the following detailed description of an embodiment thereof, with reference to the annexed drawings wherein:

DETAILED DESCRIPTION OF THE INVENTION

With reference to said figures, there is seen that the present cannula essentially consists of a straight cylindrical duct 1 from whose distal end an elliptical ogive 2 extends rearwards externally enclosing duct 1 and reaching almost the middle of the length of the latter, which is indicatively equal to 80 mm. In practice, ogive 2 would reach mid-length of duct 1 were its proximal end not cut along a plane orthogonal to the axis of duct 1 to form an internal lightening crown 2a which produces a lightening of the cannula and makes easier its molding in plastic material.

Figures 1, 2:
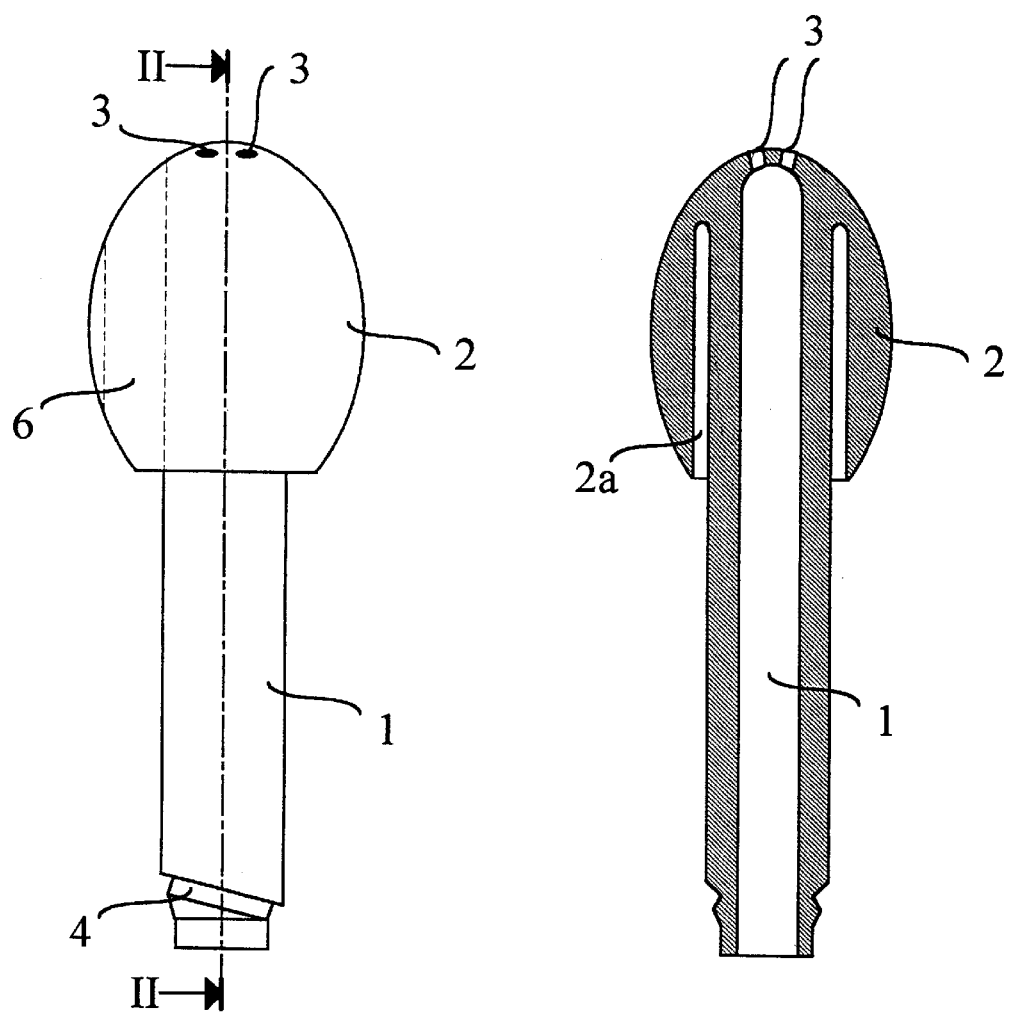
FIG. 1 is a schematic side view of the cannula.
FIG. 2 is a sectional longitudinal view along line II—II of FIG. 1.
Figure 3:
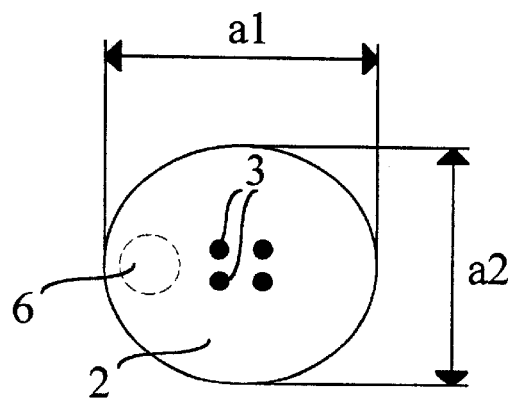
FIG. 3 is a schematic top plan view of the cannula of FIG. 1.

The duct 1 is in communication with the outside at its distal end through a ring of at least four holes 3, preferably six, having a diameter between 1 and 2 mm, preferably 1.5 mm. The holes 3 diverge outwards at an angle of 25°–35°, preferably 30°, with respect to the axis of duct 1 both in the sagittal plane and in the longitudinal plane orthogonal thereto, as shown in FIG. 2. Moreover, the plan view of FIG. 3 shows the non axial-symmetrical arrangement of holes 3 which are mutually farther along the sagittal plane than along the longitudinal plane orthogonal thereto.

This latter view also shows that, for a better anatomical shaping, ogive 2 is elliptical not only in the longitudinal plane, as clearly shown in FIGS. 1 and 2, but also in the plane orthogonal to the longitudinal axis of duct 1. In particular, the ratio between the longer axis a1 and the shorter axis a2 is 10/9 with preferential dimensions of 27 mm and 24.3 mm respectively, while duct 1 enclosed by ogive 2 has an outer diameter indicatively of 12 mm.

The proximal end of duct 1 is open and externally shaped to form a connection 4 inclined at 20°–30°, preferably 25°, in the sagittal plane with respect to the axis of duct 1. In this way, the cannula can be mounted on a bottle 5 to obtain a "curved" vaginal douche as shown in FIG. 4.

In the unlikely case that it is desired to have a short time of retention of the solution in the vaginal duct by encouraging a quick downflow thereof, it is still possible to take advantage of the anatomical shape of the present cannula by making a simple modification thereto. This modification consists of a downflow conduit 6 formed in ogive 2 parallelly to duct 1 and having about the same inner diameter of the latter, indicatively 7 mm. In this way, the liquid could flow down quickly even before the cannula is extracted from the vaginal duct.

Figure 4:
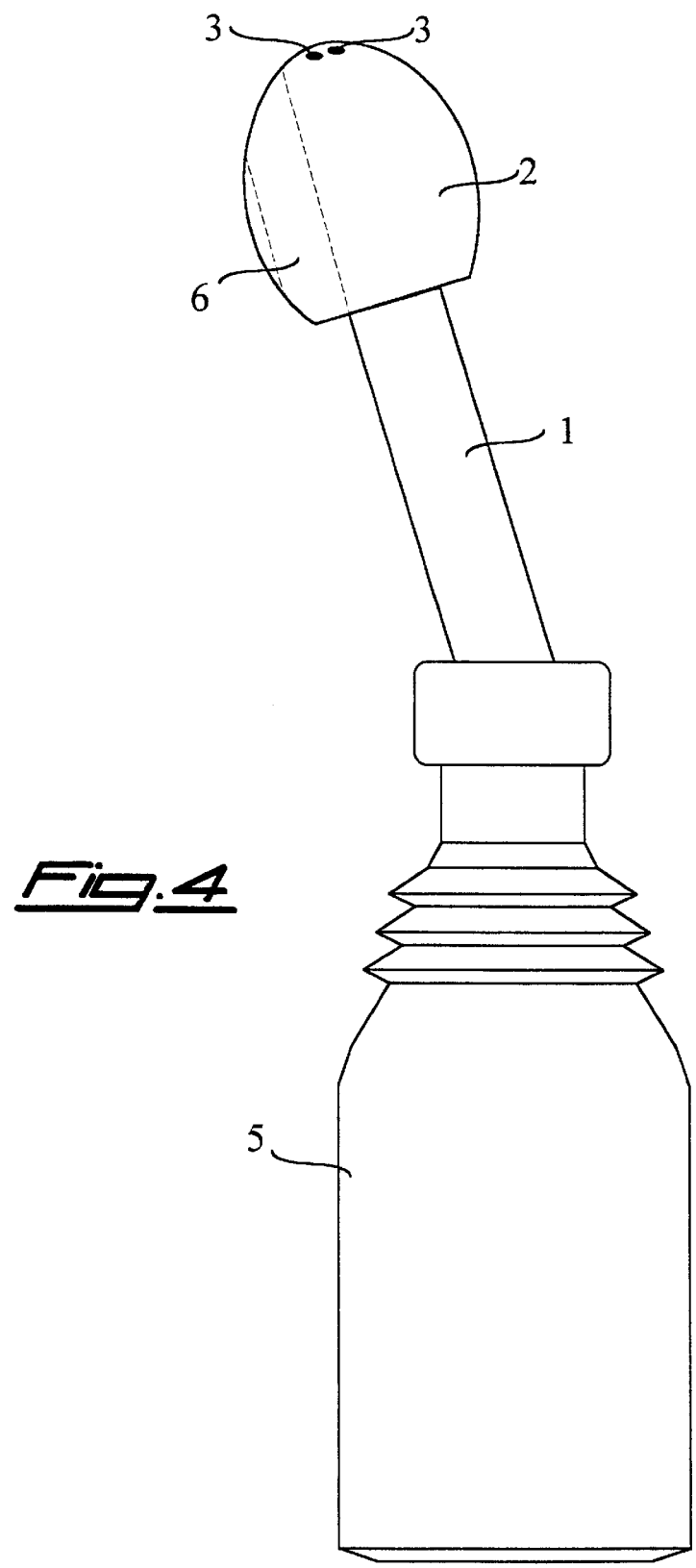
FIG. 4 is a schematic lateral view of a vaginal douche including the cannula of the preceding figures.

The conduit 6 should be formed in the sagittal plane on the side opposite with respect to the inclination of connection 4, as indicated in broken lines in FIGS. 1, 3 and 4. In this way, when the vaginal douche is correctly positioned in the vaginal duct with the tip of the cannula pointing downwards, conduit 6 is located on the lower side, i.e. close to the rear vaginal wall along which the liquid flows out.

Clearly, connection 4 for the mounting on bottle 5 may be of any kind (snap-in, bayonet, screw, etc.) and could also be not inclined with respect to the axis of duct 1. Similarly, the cannula according to the present invention can be used for vaginal irrigations with solutions supplied from any type of container different from bottle 5. For example, the cannula can be mounted at the end of the tube of a "gravity" vaginal douche, i.e. of the type consisting of an open bag-like container from whose bottom the supplying tube branches out.

Furthermore it is obvious that small dimensional and/or shape modifications may be made to the above-described embodiment of the cannula without departing from the scope of protection of the invention. In particular, the number, arrangement and inclination of holes 3 may be somewhat changed, possibly making them also with a non-circular shape and/or an axial-symmetrical arrangement.

What is claimed is:

1. A cannula for vaginal irrigations including a straight cylindrical duct (1) having a proximal end which is shaped to form a connection (4) for being mounted on a supplying device containing a treating solution and a rigid ogive (2), said olive (2) having a first end and an opposing second end, said first end positioned on a distal end of said duct (1) and said second end extending toward the proximal end of said duct so as to enclose externally a distal portion of the duct (1), said distal end of said duct being in external communication through a ring of at least four holes (3) formed on a tip of said ogive (2).

2. A cannula according to claim 1, characterized in that the ogive (2) has an elliptical shape in the longitudinal plane.

3. A cannula according to claim 1, characterized in that the ogive (2) has an elliptical shape in the plane orthogonal to the longitudinal axis, with a ratio between the longer axis (a1) and the shorter axis (a2) equal to 10/9.

4. A cannula according to claim 3, characterized in that the longer axis (a1) is 27 mm long and the shorter axis (a2) is 24.3 mm long.

5. A cannula according to claim 1, characterized in that the duct (1) is 80 mm long.

6. A cannula according to claim 1, characterized in that the ogive (2) substantially extends up to the middle of the length of the duct (1).

7. A cannula according to claim 1, characterized in that the proximal end of the ogive (2) is cut along a plane orthogonal to the axis of the duct (1) and a lightening crown (2a) is formed inside the ogive (2).

8. A cannula according to claim 1, characterized in that the holes (3) have an inclination between 25° and 35°, with respect to the axis of the duct (1) both in the sagittal plane and in the longitudinal plane orthogonal to said sagittal plane.

9. A cannula according to claim 1, characterized in that the holes (3) have a diameter between 1 and 2 mm.

10. A cannula according to claim 1, characterized in that the connection (4) is formed with an inclination between 20° and 30° in the sagittal plane with respect to the axis of the duct (1).

11. A cannula according to claim 1, characterized in that a downflow conduit (6) parallel to the duct (1) is formed in the ogive (2).

12. A cannula according to claim 11, characterized in that the downflow conduit (6) has the same inner diameter of the duct (1).

13. A cannula for vaginal irrigations including a straight cylindrical duct (1) having a proximal end which is shaped to form a connection (4) for being mounted on a supplying device containing a treating solution and a substantially rigid ogive (2) extending rearwards from a distal end of said duct (1) toward the proximal end of said duct so as to enclose externally a distal portion of the duct (1), whose distal end is in external communication through a ring of at least four holes (3) formed on a tip of said ogive (2), the connection (4) is formed with an inclination between 20° and 30° in the sagittal plane with respect to the axis of the duct (1), the cannula further including a downflow conduit (6) parallel to the duct (1) formed in the ogive (2) wherein the downflow conduit (6) is formed in the sagittal plane on the side opposite with respect to the inclination of the connection (4).

14. A vaginal douche including a container (5) suitable to supply a solution for vaginal irrigations, the douche including a cannula for vaginal irrigations including a straight cylindrical duct (1) having a proximal end which is shaped to form a connection (4) for being mounted on a supplying device containing a treating solution and a rigid ogive (2), said ogive (2) having a first end and an opposing second end, said first end positioned on a distal end of said duct (1) and said second end extending toward the proximal end of said duct so as to enclose externally a distal portion of the duct (1), whose distal end is in external communication through a ring of at least four holes (3) formed on a tip of said ogive (2).

* * * * *